United States Patent
Calfee et al.

(10) Patent No.: US 10,426,196 B2
(45) Date of Patent: Oct. 1, 2019

(54) PORTABLE VAPORIZER FOR DOSING CONCENTRATE MATERIAL

(71) Applicant: GOFIRE, INC., Denver, CO (US)

(72) Inventors: Peter William Calfee, Denver, CO (US); John Jesse Woodbine, Niwot, CO (US)

(73) Assignee: GoFire, Inc., Denver, CO (US)

( * ) Notice: Subject to any disclaimer, the term of this patent is extended or adjusted under 35 U.S.C. 154(b) by 289 days.

(21) Appl. No.: 15/177,325

(22) Filed: Jun. 8, 2016

(65) Prior Publication Data

US 2016/0360790 A1    Dec. 15, 2016

Related U.S. Application Data

(60) Provisional application No. 62/173,126, filed on Jun. 9, 2015.

(51) Int. Cl.
| | |
|---|---|
| A24F 7/00 | (2006.01) |
| A24F 47/00 | (2006.01) |
| H05B 3/00 | (2006.01) |
| A61M 15/06 | (2006.01) |
| A61M 5/315 | (2006.01) |

(52) U.S. Cl.
CPC .............. *A24F 47/008* (2013.01); *A24F 7/00* (2013.01); *A61M 5/31548* (2013.01); *A61M 15/06* (2013.01); *H05B 3/0014* (2013.01)

(58) Field of Classification Search
CPC .... A24F 47/004; A24F 47/006; A24F 47/008; A24F 7/00; A61M 15/06; A61M 5/31548; A61M 5/31578
USPC ................ 604/23, 207–211; 128/200.14
See application file for complete search history.

(56) References Cited

U.S. PATENT DOCUMENTS

| | | | | |
|---|---|---|---|---|
| 1,775,947 | A * | 9/1930 | Robinson | A61M 15/00 128/203.26 |
| 8,512,297 | B2 * | 8/2013 | Veasey | A61M 5/24 604/209 |
| 8,920,383 | B2 * | 12/2014 | Enggaard | A61M 5/31553 604/207 |
| 9,770,563 | B1 * | 9/2017 | Freeman | A61M 11/04 |
| 2004/0019333 | A1 * | 1/2004 | Graf | A61M 5/31551 604/207 |
| 2006/0196518 | A1 * | 9/2006 | Hon | A24F 47/002 131/360 |

(Continued)

*Primary Examiner* — Kevin R Kruer
(74) *Attorney, Agent, or Firm* — Emanus, LLC; Willie Jacques

(57) ABSTRACT

A portable vaporizer is described herein. The portable vaporizer includes a heating assembly having a base and a heating crucible. An extension adapter is coupled to the base of the heating assembly and slidably received within the chamber body. A cartridge receiver is coupled to the chamber body and receives a cartridge therein. A plunger having a head and a threaded shaft is received within the cartridge. The threaded shaft includes a flat edge. A cover having a bore is coupled to the cartridge receiver. The threaded shaft is threadably received through the bore. A mouthpiece having a central bore is received over the threaded shaft. A detent radially extends into the central bore and engages with the flat edge of the threaded shaft. A rotation of the mouthpiece causes an axial movement of the head of the plunger within the cartridge with respect to the cover.

20 Claims, 3 Drawing Sheets

(56) References Cited

U.S. PATENT DOCUMENTS

| | | | | |
|---|---|---|---|---|
| 2009/0025721 A1* | 1/2009 | Ellwanger | ......... | A61M 15/0028 |
| | | | | 128/203.15 |
| 2013/0199528 A1* | 8/2013 | Goodman | ............... | F22B 1/282 |
| | | | | 128/203.26 |
| 2015/0367366 A1* | 12/2015 | Edwards | .................. | A23G 1/50 |
| | | | | 239/302 |
| 2016/0029699 A1* | 2/2016 | Li | ......................... | A24F 47/008 |
| | | | | 131/329 |
| 2016/0309789 A1* | 10/2016 | Thomas, Jr. | .......... | A24F 47/008 |
| 2017/0150753 A1* | 6/2017 | Macko | .................. | A24F 47/008 |

* cited by examiner

PORTABLE VAPORIZER FOR DOSING CONCENTRATE MATERIAL

RELATED APPLICATIONS

This application claims the benefit of priority to U.S. Provisional Application Ser. No. 62/173,126, filed on Jun. 9, 2015, the content of which is herein incorporated by reference in its entirety.

FIELD OF THE DISCLOSURE

The invention relates to a portable vaporizer for measured dosing of medical and recreational marijuana concentrate products, including wax, shatter, and $CO_2$ concentrates.

BACKGROUND OF THE DISCLOSURE

Portable vaporizers have been used for extraction and inhalation of the active ingredients of various plant materials. Many existing vaporizer devices rely on one-time use cartridges, which must be purchased from a manufacturer. The user has little control over concentrate strength and limited options for dosing. From a functional standpoint, many of these same devices require the concentrate material to directly contact the metal coils of the heating element which results in undesirable degradation of the active ingredient and oxidation of the coils.

There is a need in the industry for an improved construction which eliminates or substantially reduces these drawbacks.

SUMMARY OF THE DISCLOSURE

The present disclosure is directed to a portable vaporizer which utilizes a removable and refillable cartridge. A user can remove and fill the cartridge with any form and amount of concentrate material. In addition, the portable vaporizer of the present disclosure also provides control dosage of the concentrate material by rotating the mouthpiece to a desired position. As such, the portable vaporizer has the capability to deliver to the user a desired amount of the concentrate material. The portable vaporizer of the present disclosure also includes an improved heating crucible where heating coils are enclosed within the ceramic liner. This allows the heating coil to be heated without being exposed and mitigating oxidation of the heating coils. Further, the present disclosure also provides the ability to slide the heating coil relative to the cartridge to "prime" or pre-heat non-liquid forms of concentrate material. This design allows the non-liquid concentrate materials to soften and facilitate extraction of the concentrate material from the cartridge for vaporization.

More specifically, the present disclosure is directed to a portable vaporizer generally comprising a heating assembly, a power module, a chamber assembly, a removable cartridge, and a mouthpiece.

The heating assembly includes a base and a heating crucible threadably mounted on the base. The power module includes a housing and a battery disposed within the housing. When assembled, the base of the heating assembly is threadably mounted on the housing of the power module. The power module further includes a switch for selectively energizing the heating crucible.

The chamber assembly includes a chamber body having a view window, a transparent window sleeve received within the chamber body, and an extension adapter slidably received through the chamber body. A bottom end of the extension adapter is threadably mounted to the base of the heating assembly whereby the heating crucible is slidably movable within the chamber body.

A cartridge receiver has a bottom end which is threadably mounted to a top end of the chamber body. In an example, a cross-section of the cartridge receiver is one of a square, a rectangle, a circle, a polygon, and an ellipse.

A cartridge has a conical bottom wall and an aperture at an apex of the conical bottom wall. The cartridge is slidably received into the cartridge receiver from a top end and a side wall of the cartridge receiver includes slots to permit vapor to travel along outside of the cartridge up to the mouthpiece.

Dispensing or dosing of the concentrate material is accomplished with a plunger assembly which is operated by rotating the mouthpiece. The plunger assembly includes a plunger having a head that is received within the cartridge and a threaded shaft with a flat edge. The plunger assembly further includes a cover with a bore. The threaded shaft of the plunger is threadably received through the bore and the cover is threadably coupled to the cartridge receiver to form a closed vapor chamber.

The mouthpiece has a central bore and a detent extending into the central bore. A base end of the mouthpiece is slidably received over the plunger with the detent engaging the flat edge of the plunger and the base end resting on the cover. An annular cap ring is received over the mouthpiece and threadably coupled to the cover to retain the mouthpiece in place and still permit rotation thereof.

During use, the mouthpiece is rotatably movable for dosing whereby rotation of the mouthpiece causes rotation of the plunger relative to the cover and, by way of the threaded interconnection, causes a corresponding axial movement of the plunger head downwardly within the cartridge to extract concentrate through the aperture of the cartridge.

Once a desired amount of concentrate has been dosed, the user can energize the heating coil and slide the heating coil within the chamber body to vaporize the concentrate material. Vapor may pass from the chamber body up through the slots in the side wall of the cartridge receiver, up along the flat edge of the threaded shaft and through the mouthpiece.

BRIEF DESCRIPTION OF THE DRAWINGS

While the specification concludes with claims particularly pointing out and distinctly claiming particular embodiments of the instant invention, various embodiments of the invention can be more readily understood and appreciated from the following descriptions of various embodiments of the invention when read in conjunction with the accompanying drawings in which:

DETAILED DESCRIPTION

Reference will now be made in detail to specific embodiments or features, examples of which are illustrated in the accompanying drawings. Wherever possible, corresponding or similar reference numbers will be used throughout the drawings to refer to the same or corresponding parts. Moreover, references to various elements described herein, are made collectively or individually when there may be more than one element of the same type. However, such references are merely exemplary in nature. It may be noted that any reference to elements in the singular may also be construed to relate to the plural and vice-versa without limiting the scope of the disclosure to the exact number or type of such elements unless set forth explicitly in the appended claims.

Figure 1:
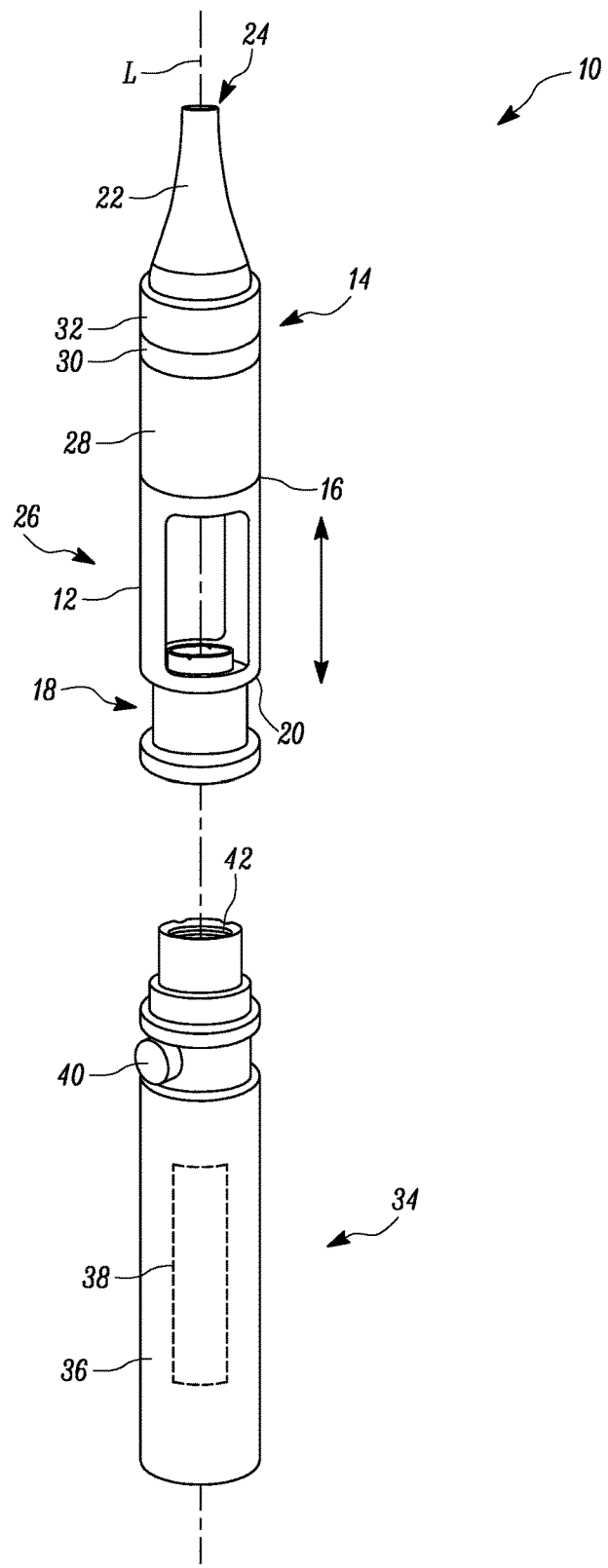
FIG. 1 is a perspective view of a portable vaporizer, according to an embodiment of the present disclosure.

A portable vaporizer 10, according to an embodiment of the present disclosure, is illustrated in detail with reference to FIGS. 1 to 3. The portable vaporizer 10 includes a chamber body 12, a plunger assembly 14 coupled to a first end 16 of the chamber body 12, and a heating assembly 18 coupled to a second end 20 of the chamber body 12. The portable vaporizer 10 further includes a mouthpiece 22 coupled to the plunger assembly 14. Vapor form of concentrate material is injected to a user through the mouthpiece 22. The mouthpiece 22 is tapered towards a supply end 24 thereof to facilitate injection of the vapor form of the concentrate material to a mouth of the user. The portable vaporizer 10 further includes a chamber assembly 26, which includes the chamber body 12. The portable vaporizer 10 further includes a cartridge receiver 28 coupled to the first end 16 of the chamber body 12. The plunger assembly 14 includes a cover 30 coupled to the cartridge receiver 28. The cover 30 supports various components of the plunger assembly 14 within the chamber assembly 26. The mouthpiece 22 is disposed on the cover 30, and an annular cap ring 32 of the portable vaporizer 10 is received over the mouthpiece 22 and coupled to the cover 30. The heating assembly 18, the chamber assembly 26, the cartridge receiver 28, the cover 30, the annular cap ring 32, and the mouthpiece 22 are coupled in a coaxial manner, such as along a longitudinal axis 'L' of the portable vaporizer 10. The heating assembly 18 is movable within the chamber assembly 26 along the longitudinal axis 'L' of the portable vaporizer 10.

The portable vaporizer 10 further includes a power module 34. The power module 34 includes a housing 36 and a power source 38 disposed within the housing 36. In one embodiment, the power source 38 includes one of a battery and a fuel cell. In another embodiment, the power source 38 may be adapted to communicate with external power supply to energize the portable vaporizer 10. In the present embodiment, a cross-section of an outer periphery of the housing 36 is a circle. However, in some embodiments, the cross-section of the outer periphery of the housing 36 may be one of a polygon and an ellipse. The power module 34 also includes a switch 40 provided on the housing 36. Further, the switch 40 is in electronic communication with the power source 38 to selectively energize the heating assembly 18. For the purpose of illustration, the switch 40 is shown as a button provided on the housing 36. As such, the switch 40 can be easily accessible by the user of the portable vaporizer 10. It may be contemplated that the switch 40 may be provided in any other manner in the housing 36 to selectively energize the heating assembly 18. The power module 34 further includes a receptacle 42 adapted to couple with the heating assembly 18 and, therefore, aids in removably coupling the power module 34 with the heating assembly 18. In an embodiment, electrical connections may be formed through the receptacle 42 (standard 5/10 adapter). In some embodiments, the power module 34 may include a control module and a display for displaying a value of current and voltage in the power source 38. The control module may allow the user to control the current and the voltage by actuating one or more control buttons that may be provided in the housing 36. In the present embodiment, the heating assembly 18 is threadably coupled to the receptacle 42 of the housing 36. In some embodiments, the heating assembly 18 may be coupled to the receptacle 42 of the housing 36 by a snap fit or any other coupling methods known in the art.

Figure 2:
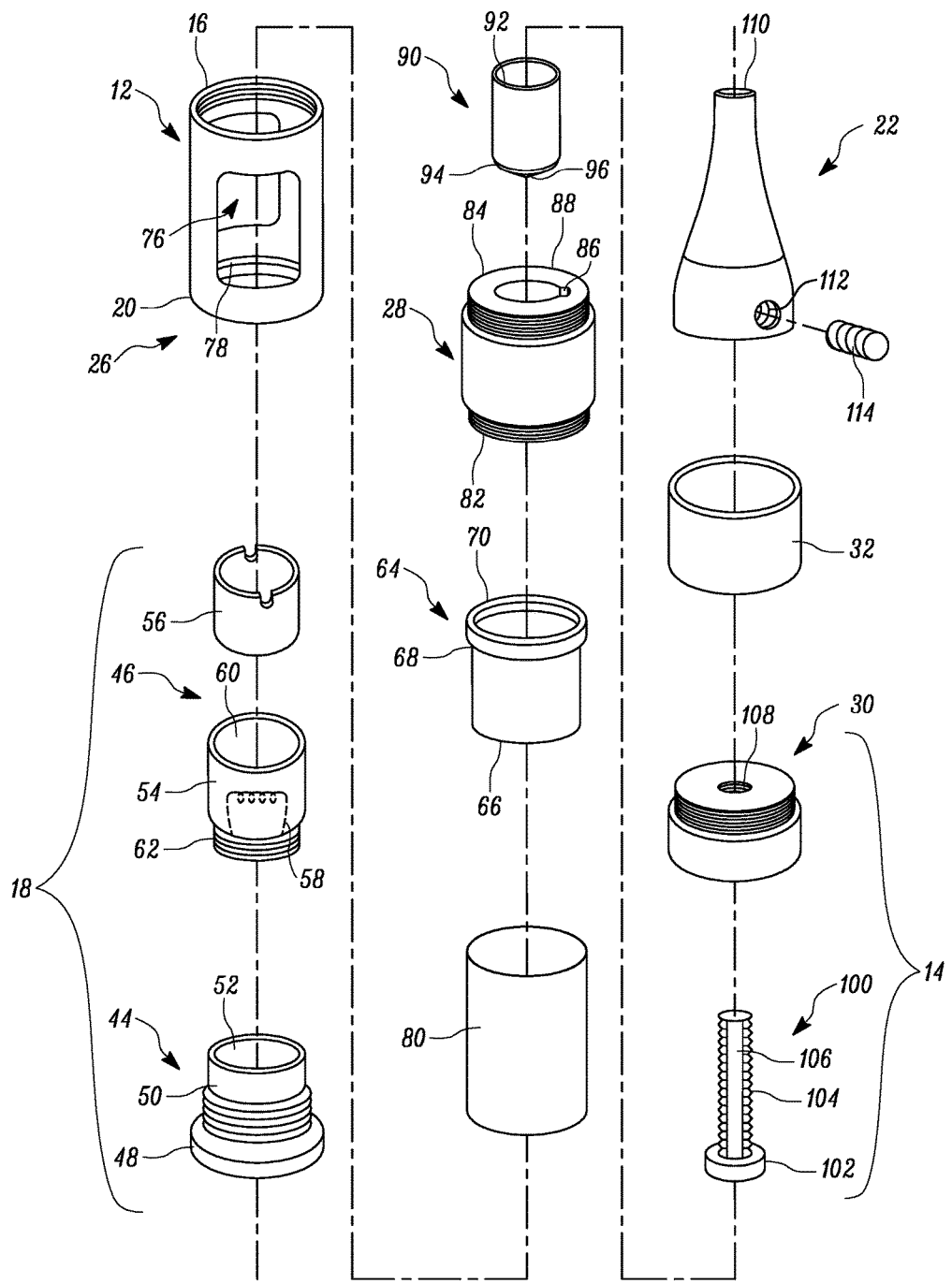
FIGS. 2 and 3 are exploded perspective views of the portable vaporizer from different angles, according to an embodiment of the present disclosure.
Figure 3:
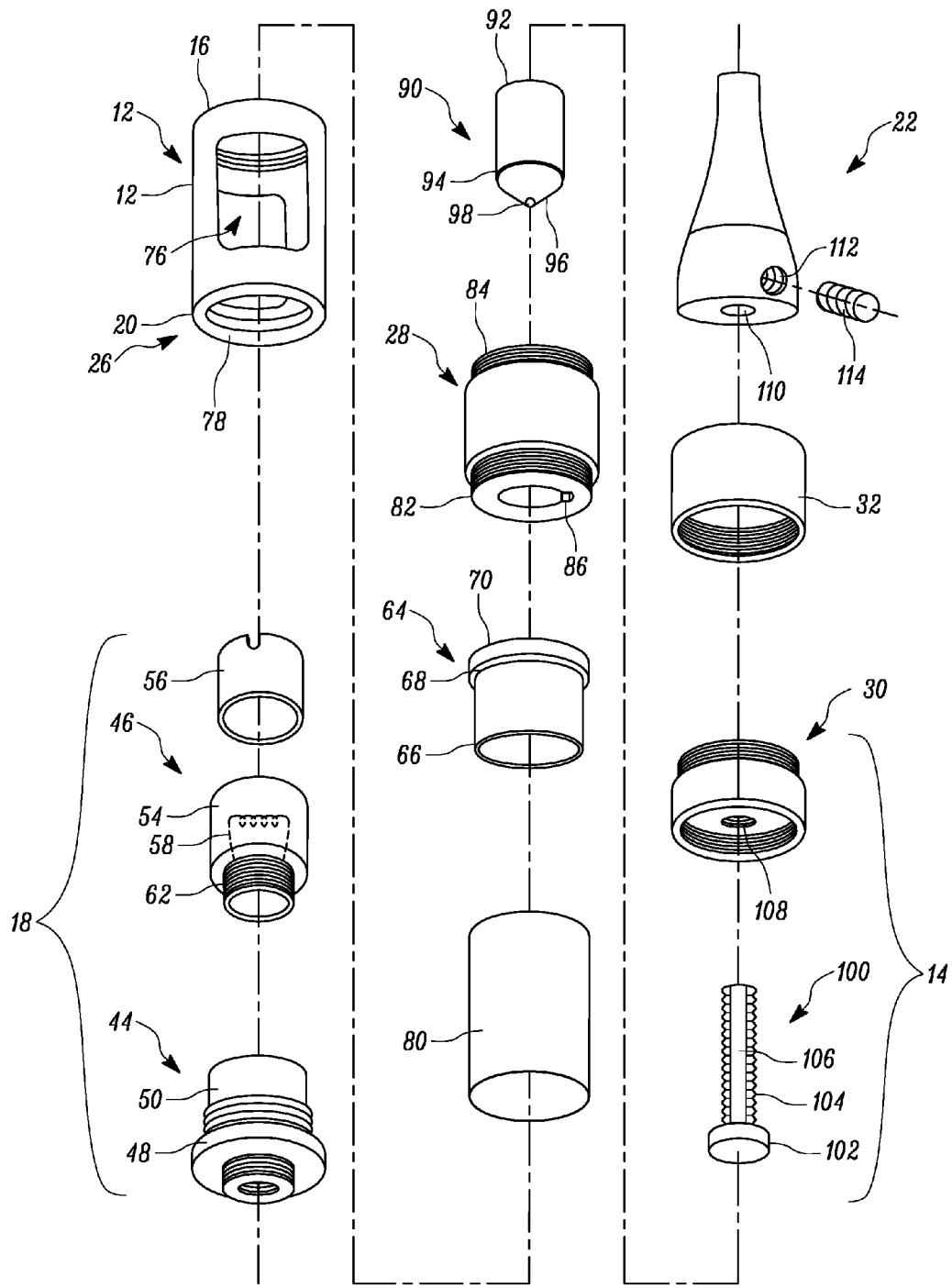

An exploded perspective view of the portable vaporizer 10 from two different angles is illustrated in each of FIG. 2 and FIG. 3. In particular, FIG. 2 and FIG. 3 also illustrate a manner in which each component can be coupled to an adjacent component to constitute the portable vaporizer 10. The heating assembly 18 includes a base 44 and a heating crucible 46 coupled to the base 44. The base 44 includes a seat 48 and a shoulder 50 that extends from the seat 48. In the illustrated example, a cross-section of an outer periphery of the seat 48 is a circle. However, in other examples, the cross-section of the outer periphery of the seat 48 may be one of a polygon and an ellipse. An outer surface of the shoulder 50 is provided with threads, as shown in FIG. 2. Further, the shoulder 50 includes a bore 52 and fastening threads (not shown) which are formed at an inner surface of the bore 52.

The heating crucible 46 includes a main body portion 54 and a ceramic liner 56. A heating coil 58 is provided within a bore 60 of the main body portion 54. An inner diameter of the bore 60 of the main body portion 54 is greater than an outer diameter of the ceramic liner 56. As such, the ceramic liner 56 is coaxially received within the main body portion 54. In an example, the ceramic liner 56 may be completely inserted into the bore 60 of the main body portion 54 or may be partially received within the bore 60. In the illustrated example, a cross-section of each of the main body portion 54 and the ceramic liner 56 is a circle. However, in some embodiments, the cross-section of each of the main body portion 54 and the ceramic liner 56 may be a polygon. The main body portion 54 further includes a protrusion 62 having threads formed thereon. An outer diameter of the threads provided on the protrusion 62 is defined based on an inner diameter of the bore 52 of the shoulder 50. Accordingly, the main body portion 54 is threadably coupled to the base 44.

The chamber assembly 26 includes an extension adapter 64 having a first end 66 and a second end 68. A flange 70 is provided at the second end 68 of the extension adapter 64. The extension adapter 64 is formed as a hollow cylindrical component. In the present embodiment, the first end 66 of the extension adapter 64 is provided with internal threads. Accordingly, the extension adapter 64 is threadably coupled to the base 44 of the heating assembly 18. Specifically, the internal threads of the extension adapter 64 can engage with the threads formed on the outer surface of the shoulder 50 of the base 44. Further, an inner diameter of the extension adapter 64 can be predefined based on an outer diameter of the main body portion 54 of the heating crucible 46, such that the main body portion 54 can be coaxially disposed within the extension adapter 64. In an example, the heating crucible 46 may be partially concealed within the extension adapter 64.

The extension adapter 64 is slidably received within the chamber body 12. In the present embodiment, the chamber body 12 is formed as a hollow tubular component. In some embodiments, a cross-section of an outer periphery of the chamber body 12 may be a polygon. The chamber body 12 includes a view window 76 defined between the first end 16 and the second end 20. In the illustrated example, a pair of view windows 76 is provided in the chamber body 12. Further, a seating 78 is provided at the second end 20. The seating 78 is provided as a flange 70 that extends internally with respect to an inner surface of the chamber body 12. The chamber assembly 26 further includes a transparent window sleeve 80. An outer diameter of the transparent window sleeve 80 is less than an inner diameter of the chamber body 12. As such, the transparent window sleeve 80 can be coaxially received within the chamber body 12. Further, the transparent window sleeve 80 may be attached to the inner surface of the chamber body 12 by adhesive. The transparent window sleeve 80 allows the user to see through the chamber body 12 through the view windows 76.

The extension adapter 64 can be coaxially inserted through the chamber body 12 until the flange 70 of the extension adapter 64 is restricted by the seating 78 of the chamber body 12. Accordingly, the extension adapter 64 is movably received within the chamber body 12. As described above, the extension adapter 64, along with the heating crucible 46, may be coupled to the base 44. Therefore, the heating assembly 18 can be moved along the longitudinal axis 'L' with respect to the chamber body 12.

The portable vaporizer 10 further includes the cartridge receiver 28 having a first end 82 and a second end 84. Both the first and second ends 82, 84 are provided with external threads. The cartridge receiver 28 may be coaxially positioned with respect to the chamber body 12. Upon positioning, the cartridge receiver 28 can be moved towards the first end 16 of the chamber body 12 to couple the cartridge receiver 28 with the chamber body 12. The first end 16 of the chamber body 12 is provided with internal threads to engage with the external threads at the first end 82 of the cartridge receiver 28. The cartridge receiver 28 also includes a slot 86 formed in a side wall 88 thereof. In some embodiments, a plurality of slots 86 may be defined at an inner surface of the side wall 88. In the present embodiment, a cross-section of an outer periphery of the cartridge receiver 28 is a circle. In some embodiments, the cross-section of the outer periphery of the cartridge receiver 28 may be a polygon or an ellipse.

The portable vaporizer 10 further includes a cartridge 90 having a top end 92 and a bottom end 94. The cartridge 90 is adapted to receive and store the concentrate material. In an example, the concentrate material may be in the form of powder or liquid. As such, the cartridge 90 is formed as a hollow container and the bottom end 94 includes a conical bottom wall 96. An aperture 98 is formed at an apex of the conical bottom wall 96. An outer diameter of the cartridge 90 is less than an inner diameter of the cartridge receiver 28. As such, the cartridge 90 can be coaxially received within the cartridge receiver 28.

The portable vaporizer 10 further includes the plunger assembly 14 having a plunger 100 and the cover 30. The plunger 100 includes a head 102 and a threaded shaft 104 extending from the head 102. The threaded shaft 104 includes a flat edge 106. An outer diameter of the head 102 of the plunger 100 is less than an inner diameter of the cartridge 90. As such, the plunger 100 can be slidably received within the cartridge 90. Further, the cover 30 includes a bore 108 for coaxially receiving the threaded shaft 104 of the plunger 100 therethrough. The cover 30 is coupled to the cartridge receiver 28. In particular, the cover 30 is threadably coupled to the second end 84 of the cartridge receiver 28.

The mouthpiece 22 includes a central bore 110 and a radial hole 112 extending from an outer surface of the mouthpiece 22 until the central bore 110. The threaded shaft 104 of the plunger 100 is received within the central bore 110 of the mouthpiece 22. Further, a detent 114 is threadably received within the radial hole 112. In an assembled condition of the mouthpiece 22 and the plunger assembly 14, the detent 114 engages with the flat edge 106 of the threaded shaft 104. The portable vaporizer 10 further includes the annular cap ring 32 received over the mouthpiece 22 and threadably coupled to the cover 30 to retain the mouthpiece 22 in position.

In order to use the portable vaporizer 10, the user may fill the cartridge 90 with the concentrate material and assemble the portable vaporizer 10 in a manner as described above. The cartridge 90 may be filled, and re-filled, with any concentrate material in any form, such as wax, shatter, $CO_2$ concentrates, powder or liquid. Once the portable vaporizer 10 is assembled, the mouthpiece 22 may be rotated. Since the detent 114 is engaged with the flat edge 106 of the threaded shaft 104, the detent 114 restricts individual rotation of the threaded shaft 104. However, the detent 114 aids in retaining the threaded shaft 104 along with the mouthpiece 22 while rotating. Accordingly, the threaded shaft 104 rotates with the mouthpiece 22. Since the threaded shaft 104 is threadably engaged with the cover 30 and the cover 30 is stationary during rotation of the mouthpiece 22, the threaded shaft 104 experiences an axial movement thereof. As such, the head 102 of the plunger 100 moves towards the bottom end 94 of the cartridge 90, thereby forcing the concentrate material out of the cartridge 90 through the aperture 98. Through the view window 76, the user may view amount of the concentrate material being forced through the aperture 98, and may accordingly control the rotation of the mouthpiece 22. For instance, a small degree of rotation of the mouthpiece 22 may cause a small amount of the concentrate material to be forced through the aperture 98. Likewise, a high degree of rotation of the mouthpiece 22 may allow large amount of the concentrate material to be forced through the aperture 98. As such, desired amount or dose of the concentrate material may also be controlled. In an embodiment, the outer surface of the mouthpiece 22 may have a set of markings engraved thereon and a single marking may be engraved on the annular cap ring 32. Alignment of each of the set of markings with the single marking on the annular cap ring 32 can indicate dosing of a particular amount of the concentrate material. In such cases, the user may dose a required amount of the concentrate material as per a medical prescription.

The heating crucible 46 can be moved within the chamber body 12 to a position adjacent to the aperture 98 to warm and soften or liquefy the concentrate material dosed therein. This is called a "primer" effect. Softening makes the concentrate material easier to extract through the aperture 98. The ceramic liner 56 disposed around the heating coil 58 isolates the heating coil 58 from the concentrate material. As such, the heating coil 58 may be heated by the power module 34 without being exposed and mitigating oxidation of the heating coil 58. The switch 40 can be accessed to energize the heating assembly 18 and thereby to heat the concentrate material dosed within the chamber body 12. Upon energizing of the heating assembly 18, the dosed concentrate material takes a vapor form thereof. Such vapor form of the concentrate material travels through the slot 86 provided in the side wall 88 of the cartridge receiver 28. Vapor formation from the concentrate material will be based on amount of concentrate material dosed. Further, the vapor passes through a clearance (not shown) defined by the flat edge 106 of the threaded shaft 104 within the bore 108 and then through the central bore 110 of the mouthpiece 22. Thus, the vapor travels upwards and towards the mouthpiece 22 for being injected to the user.

While there is shown and described herein certain specific structures embodying various embodiments of the invention, it will be manifest to those skilled in the art that various modifications and rearrangements of the parts may be made without departing from the spirit and scope of the underlying inventive concept and that the same is not limited to the particular forms herein shown and described except insofar as indicated by the scope of the appended claims.

LIST OF ELEMENTS

10 Portable vaporizer
12 Chamber body
14 Plunger assembly
16 First end of chamber body
18 Heating assembly
20 Second end of chamber body
22 Mouthpiece
24 Supply end
26 Chamber assembly
28 Cartridge receiver
30 Cover
32 Annular cap ring
34 Power module
36 Housing
38 Power source
40 Switch
42 Receptacle
44 Base
46 Heating crucible
48 Seat
50 Shoulder
52 Bore of base
54 Main body portion
56 Ceramic liner
58 Heating coil
60 Bore of main body portion
62 Protrusion
64 Extension adapter
66 First end of extension adapter
68 Second end of extension adapter
70 Flange
76 View window
78 Seating
80 Transparent window sleeve
82 First end of cartridge receiver
84 Second end of cartridge receiver
86 Slot
88 Side wall
90 Cartridge
92 Top end of cartridge
94 Bottom end of cartridge
96 Conical bottom wall
98 Aperture
100 Plunger
102 Head
104 Threaded shaft
106 Flat edge
108 Bore of cover
110 Central bore
112 Radial hole
114 Detent
L Longitudinal axis

What is claimed is:

1. A portable vaporizer comprising:
a heating assembly including a base and a heating crucible coupled to the base;
a chamber assembly having a chamber body adapted to slidably receive an extension adapter therein, the extension adapter being coupled to the base of the heating assembly;
a cartridge receiver having a slot in a side wall thereof being coupled to the chamber body;
a cartridge having an aperture at a bottom end thereof being received within the cartridge receiver;
a plunger having a head and a threaded shaft extending from the head being slidably received within the cartridge, wherein the threaded shaft includes a flat edge;
a cover having a bore being coupled to the cartridge receiver, wherein the threaded shaft is threadably received through the bore; and
a mouthpiece having a central bore being slidably received over the threaded shaft, the mouthpiece including a detent radially extending into the central bore, and engaging with the flat edge of the threaded shaft of the plunger, wherein a rotation of the mouthpiece causes an axial movement of the head of the plunger within the cartridge with respect to the cover.

2. The portable vaporizer of claim 1, wherein the heating crucible includes a main body portion having a heating coil and a ceramic liner disposed within the main body portion around the heating coil.

3. The portable vaporizer of claim 1 further comprising a power module including a housing, and a power source within the housing, wherein the base of the heating assembly is coupled to the housing of the power module.

4. The portable vaporizer of claim 3, wherein the power module includes a switch disposed on the housing and in electronic communication with the power source to selectively energize the heating crucible.

5. The portable vaporizer of claim 4, wherein the power source comprises at least one of a battery and a fuel cell.

6. The portable vaporizer of claim 1 further comprising an annular cap ring received over the mouthpiece and coupled to the cover, wherein the annular cap ring is adapted to retain the mouthpiece in position.

7. The portable vaporizer of claim 1, wherein the chamber body includes a view window, and wherein the chamber assembly includes a transparent window sleeve received within the chamber body.

8. The portable vaporizer of claim 1, wherein a cross-section of an outer periphery of each of the chamber body, the cartridge receiver, and the cover is one of a circle, a polygon, and an ellipse.

9. A portable vaporizer comprising:
a heating assembly including a base and a heating crucible coupled to the base;
a power module including a housing and a power source within the housing, the housing being coupled to the base of the heating assembly;
a chamber assembly having a chamber body adapted to slidably receive an extension adapter therein, the extension adapter being coupled to the base of the heating assembly and disposed around the heating crucible;
a cartridge receiver having a slot in a side wall thereof being coupled to the chamber body;
a cartridge having an aperture at a bottom end thereof being received within the cartridge receiver;
a plunger having a head and a threaded shaft extending from the head being slidably received within the cartridge, wherein the threaded shaft includes a flat edge;
a cover having a bore being coupled to the cartridge receiver, wherein the threaded shaft is threadably received through the bore;
a mouthpiece having a central bore being slidably received over the threaded shaft, the mouthpiece including a detent radially extending into the central bore, and engaging with the flat edge of the threaded shaft of the plunger, wherein a rotation of the mouthpiece causes an axial movement of the head of the plunger within the cartridge with respect to the cover; and an annular cap ring received over the mouthpiece and coupled to the cover, wherein the annular cap ring is adapted to retain the mouthpiece in position.

10. The portable vaporizer of claim 9, wherein the heating crucible includes a main body portion having a heating coil and a ceramic liner disposed within the main body portion around the heating coil.

11. The portable vaporizer of claim 9, wherein the power module includes a switch disposed on the housing and in electronic communication with the power source to selectively energize the heating crucible.

12. The portable vaporizer of claim 11, wherein the power source comprises at least one of a battery and a fuel cell.

13. The portable vaporizer of claim 9, wherein the chamber body includes a view window, and wherein the chamber assembly includes a transparent window sleeve received within the chamber body.

14. The portable vaporizer of claim 9, wherein the extension adapter is threadably mounted on the base of the heating assembly and includes a flange configured to retain the extension adapter within the chamber body.

15. The portable vaporizer of claim 9, wherein the cartridge includes a conical bottom wall at the bottom end thereof and the aperture is located at an apex of the conical bottom wall.

16. The portable vaporizer of claim 9, wherein the cartridge receiver is threadably coupled to the chamber body.

17. The portable vaporizer of claim 9, wherein the cover is threadably coupled to the cartridge receiver.

18. The portable vaporizer of claim 9, wherein the annular cap ring is threadably coupled to the cover.

19. The portable vaporizer of claim 9, wherein a cross-section of an outer periphery of each of the chamber body, the cartridge receiver, the cover, and the annular cap ring is one of a circle, a polygon, and an ellipse.

20. A portable vaporizer comprising:
a heating assembly including a base and a heating crucible threadably coupled to the base, the heating crucible including a main body portion having a heating coil and a ceramic liner disposed within the main body portion around the heating coil;
a power module including a housing, a battery within the housing, and a switch disposed on the housing and in electronic communication with the battery, wherein the housing of the power module is threadably coupled to the base of the heating assembly;
a chamber assembly including a chamber body having a view window, a transparent window sleeve received within the chamber body, and an extension adapter slidably received within the chamber body, the extension adapter being threadably coupled to the base of the heating assembly and disposed around the main body portion of the heating crucible;
a cartridge receiver having a slot in a side wall thereof being threadably coupled to the chamber body;
a cartridge including a conical bottom wall and an aperture at an apex of the conical bottom wall, the cartridge being received within the cartridge receiver;
a plunger assembly including:
a plunger having a head slidably received within the cartridge and a threaded shaft extending from the head, wherein the threaded shaft includes a flat edge; and
a cover having a bore being threadably coupled to the cartridge receiver, wherein the threaded shaft of the plunger is threadably received through the bore;
a mouthpiece having a central bore being slidably received over the threaded shaft, the mouthpiece including a detent radially extending into the central bore, and engaging with the flat edge of the threaded shaft of the plunger, wherein a rotation of the mouthpiece causes an axial movement of the head of the plunger within the cartridge with respect to the cover; and
an annular cap ring received over the mouthpiece and threadably coupled to the cover, wherein the annular cap ring is adapted to retain the mouthpiece in position.

\* \* \* \* \*